US005666946A

United States Patent [19]

Langenback

[11] Patent Number: 5,666,946
[45] Date of Patent: Sep. 16, 1997

[54] APPARATUS FOR DELIVERING DRUGS TO THE LUNGS

[75] Inventor: Edward G. Langenback, Bellport, N.Y.

[73] Assignee: Respirogenics Corporation, Bellport, N.Y.

[21] Appl. No.: 632,964

[22] Filed: Apr. 16, 1996

Related U.S. Application Data

[63] Continuation of Ser. No. 274,238, Jul. 13, 1994, abandoned.

[51] Int. Cl.[6] ..................... A61M 11/00

[52] U.S. Cl. ..................... 128/200.16; 128/204.25; 128/203.12; 128/204.18; 128/200.14

[58] Field of Search ..................... 128/200.14, 200.16, 128/203.12, 203.24, 204.14, 200.18, 200.21, 209.18, 204.24, 204.25, 204.26, 204.27, 205.24

[56] References Cited

U.S. PATENT DOCUMENTS

| | | | |
|---|---|---|---|
| 4,279,250 | 7/1981 | Valenta et al. | 128/200.14 |
| 4,456,008 | 6/1984 | Clawson et al. | 128/204.25 |
| 4,592,349 | 6/1986 | Bird | 128/204.25 |
| 4,823,784 | 4/1989 | Bordoni et al. | 128/200.14 |
| 4,838,257 | 6/1989 | Hatch | 128/204.18 |
| 5,080,093 | 1/1992 | Raabe et al. | 128/204.17 |
| 5,322,057 | 6/1994 | Raabe et al. | 128/203.12 |
| 5,388,571 | 2/1995 | Roberts et al. | 128/203.12 |

*Primary Examiner*—Vincent Millin
*Assistant Examiner*—William J. Deane, Jr.
*Attorney, Agent, or Firm*—Brumbaugh, Graves, Donohue & Raymond

[57] ABSTRACT

Apparatus for delivering drugs to the lungs from an ultrasonic nebulizer by inspiration using a ventilator includes a flow system in which the nebulizer is connected in parallel with the series conduit between the ventilator delivery outlet and the ventilator discharge valve and exhaust outlet. One-way valves in parallel flow conduits to the nebulizer provide for bypassing the nebulizer except when the ventilator is in the inspiration phase of its operation, thereby eliminating an important cause of loss of drugs to the ventilator outlet during the expiration phase. The nebulizer, which can also be used for administration of drugs by inhalation (without a ventilator) has a flow regulator which provides for delivery of the drug from the nebulizer only during part of inspiration (or inhalation in a mouth breathing use) and for delivery of gas (air or oxygen) during the remaining part of inspiration (inhalation). A cone in the cap above the vibrating crystal of an ultrasonic nebulizer and improved inlet and outlet porting in the cap improve the conditions in the aerosol chamber of the nebulizer cap to enhance efficiency of drug delivery and reduce drug losses.

32 Claims, 8 Drawing Sheets

APPARATUS FOR DELIVERING DRUGS TO THE LUNGS

This application is a continuation of application Ser. No. 08/274,238, filed on Jul. 13, 1994 now abandoned.

BACKGROUND OF THE INVENTION

The delivery of drugs by aerosolization to neonates and infants who are breathing on a ventilator (mechanically ventilated) has been problematic and unsuccessful. The inherent properties of the ventilator and the nebulizer have contributed to the inefficacious drug delivery. Nebulizers are devices which create aerosolized particles for inhalation. These particles are usually composed of water droplets containing dissolved drugs. However, the particles may be lipid or other types of liquid droplets or dry.

Inhalation is considered the best method for drug delivery to the lung and possibly the heart. Drugs delivered by inhalation are targeted directly to the lung, permitting much lower doses for effect in the lung than if given systemically. Inhalation is the natural route to the lung, permitting homogeneous distribution of drugs in the lung with an even application of dose. Despite a general agreement that inhalation is the best route of drug administration, attempts to administer aerosol drugs to mechanically ventilated or spontaneously breathing infants have been unsuccessful. Even efforts to produce aerosols for inhalation by children and adults have not met with great success. Less than 2% of drugs put in nebulizers deposit in the lungs of mechanically ventilated or spontaneously breathing infants. A range between 5% and 20% of drugs in the nebulizers reach the lungs of children or adults.

Nebulizers of various designs are used for administering drugs. One type of nebulizer that is widely used is an ultrasonic nebulizer. A vibrating crystal in the bottom of a vessel that contains the drug in solution can produce an aerosol of droplets about 1 to 5 microns in diameter contained in a chamber (cap) above the liquid. Ultrasonic nebulizers can be used with a mouthpiece for inhalation by natural breathing or can be connected to a ventilator for administration through an endotracheal tube. In the case of inhalation, a portion of the inhaled aerosol is exhaled from the lungs, rather than being deposited on the surfaces of the lungs. In mechanically ventilated infants, a large fraction of the drug is also lost upon expiration and by adhesion to the cap and deposition on the surfaces of the hoses of the ventilator and the endotracheal tube.

Infant ventilators are continuous flow ventilators. This means that air or oxygen continually flows through the ventilator when the exhalation valve is open. If the number of breaths per minute is set at 30 and the inspiration time is set at 0.5 sec. (common ventilator settings for infants) the expiration time is 1.5 seconds. During this 1.5 seconds gas flows through the ventilator continuously. If the nebulizer is positioned directly in line with the ventilator tubing (in. series), gas will blow through the nebulizer, wasting the aerosolized drug that flows through the ventilator tube and out though the outlet valve of the ventilator during expiration and rest.

SUMMARY OF THE INVENTION

One object of the present invention is to provide apparatus for administration of drugs to the lungs that greatly increases the proportion of the drugs deposited on the surfaces of the lungs for a given amount of drug solution, as compared with presently known administration apparatus. Another object is to provide a nebulizer cap and an associated flow system that provide greatly improved efficacy of administration, that can be produced at low cost, and that can be used to administer a large variety of drugs, via mechanical ventilation or natural breathing. The concepts of the present invention are adaptable, in particular, to commercially available ultrasonic nebulizers.

More particularly, there is provided, in accordance with one aspect of the present invention, apparatus for delivering drugs to the lungs comprising a ventilator having a gas delivery outlet and a gas return inlet, a series conduit leading from the ventilator outlet to the gas return inlet, a return gas outlet valve at the gas return inlet, and an ultrasonic nebulizer adapted to form an aerosol from a solution of a drug and having a cap that defines a chamber for the aerosol and having an inlet and an outlet. A first conduit is connected between the series conduit and the nebulizer cap inlet and has a one-way valve that permits gas to flow only from the series conduit to the nebulizer inlet. A second conduit is connected between the nebulizer cap outlet and the series conduit at a location downstream, with respect to the direction of gas flow through the series conduit from the ventilator delivery outlet, from the connection between the first conduit and the series conduit. The second conduit has a one-way valve that permits gas to flow only from the nebulizer cap to the series conduit. An endotracheal tube is connected between the cap outlet and the lungs and communicates with the second conduit upstream from the one-way valve in the second conduit, with respect of the direction of gas flow to the series conduit.

A pressure sensor conduit is connected between the second conduit at a location upstream from the one-way valve in the second conduit, with respect of the direction of gas flow to the series conduit, and a pressure transducer in the ventilator that operates the return gas outlet valve.

In accordance with the first aspect of the invention, the passage through the nebulizer is in parallel with the series passage of the ventilator, and the two one-way valves allow gas to flow through the nebulizer only during inspiration. Accordingly, one of the major sources of loss of drugs, namely, exhaust through the ventilator during rest and expiration, is eliminated. Also, losses of the drug through deposit in the tubing walls is significantly reduced.

A second aspect of the invention involves delivery of the drug aerosol to the lungs during only part of the inspiration and delivering air or oxygen (a gas without the drug aerosol) during the remainder of the inspiration. A bypass conduit is connected to the endotracheal tube. A flow regulator controls the flow from the ventilator so that during part of the inspiration, the gas flow is through the nebulizer and during the remainder of the inspiration, the gas flow is through the bypass.

If the drug aerosol is targeted to the lungs, the flow regulator is set up to provide inspiration flow through the nebulizer during the initial part of the inspiration, and the flow through the bypass in the final part of inspiration drives the drug aerosol deeply into the lungs. This aspect of the invention greatly reduces another cause for a high loss of the drug, expulsion of aerosolized drug upon expiration. The regulator can also be set up to provide inspiration of gas only through the bypass during an initial portion of inspiration, followed by drug aerosol delivery during the final part of inspiration. In this case, the drug is targeted to the bronchial airways (upper areas of the lung), which may be the treatment desired for the patient's condition. The regulator has two outlets and a valve to switch between them, and changing from one mode to the other requires only connecting the two outlets to the desired flow paths—one to the nebulizer chamber and the other to the bypass.

The second aspect of the invention, regulation of delivery of the drug aerosol and gas through a bypass, can be applied both for drug delivery in conjunction with a ventilator (inspiration) and by natural inhalation by the patient in normal breathing.

A third aspect of the invention relates to the nebulizer cap. The nebulizer cap has a wall member presenting a downwardly facing conical surface having its apex centered above a vibrating crystal of the nebulizer. The cap inlet includes a first inlet port in the conical surface of the wall member in spaced apart relation from the apex and the outlet from the cap includes an outlet port located proximate to the base of the conical surface and generally diametrically opposite from the cap inlet. The cap inlet, preferably, also includes a second inlet port located proximate to the base of the conical surface and generally diametrically opposite from the cap outlet port.

The design of the cap improves the formation of the aerosol by, causing the geyser of the drug solution to impinge on the surfaces of the conical wall, which breaks up the liquid particles and disperses them. The cap design also reduces drug losses by reducing the amount of surface area to which the aerosol is exposed in the cap. The volume of the free space in the cap is made desirably small for use in treating neonate and infants, who receive only small volumes of gases upon inspiration. The inlet, especially the dual porting, provides improved transport of the aerosol from the cap by producing a downflow and a cross-flow of gas. The cap is useful for drug administration by both inspiration with a ventilator and inhalation by natural breathing.

For a better understanding of the invention, reference may be made to the following description of exemplary embodiments, taken in conjunction with the accompanying drawings.

DESCRIPTION OF THE EMBODIMENTS

Figure 1:
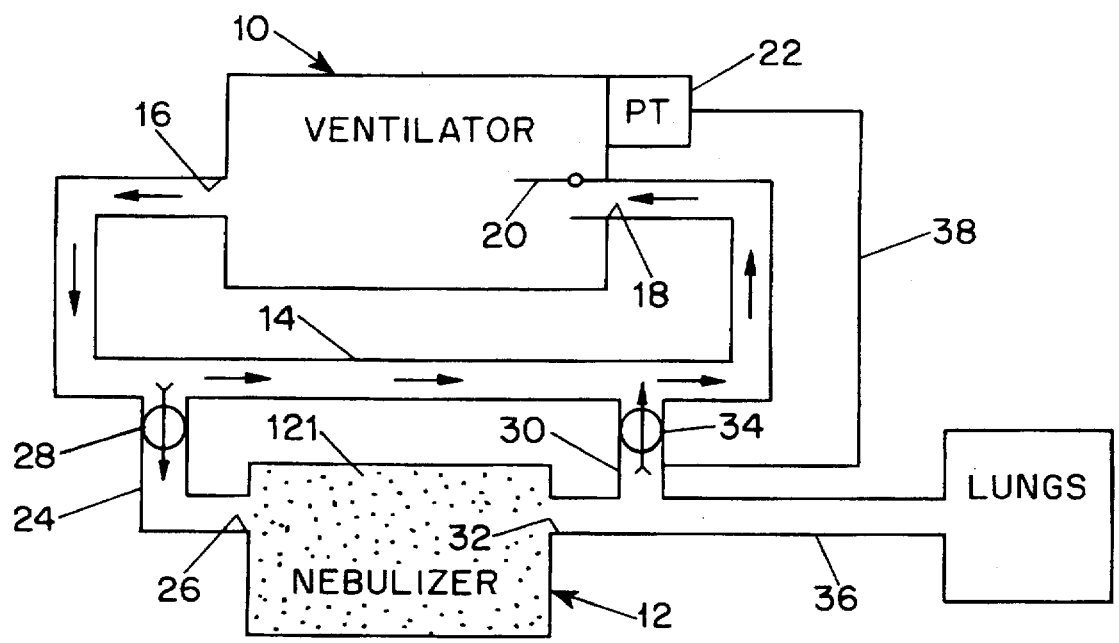
FIGS. 1 to 3 are schematic diagrams of apparatus for administering drugs to the lungs by a nebulizer connected in parallel with a continuous flow-type ventilator and show the apparatus in different phases of its operation.
Figure 2:
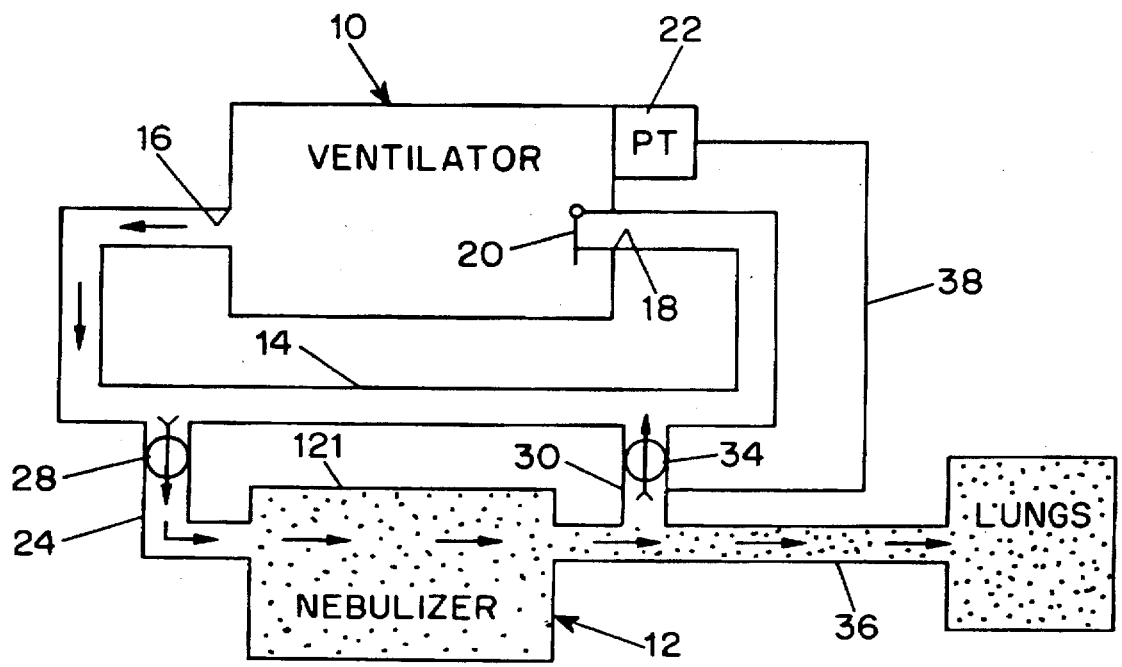
Figure 3:
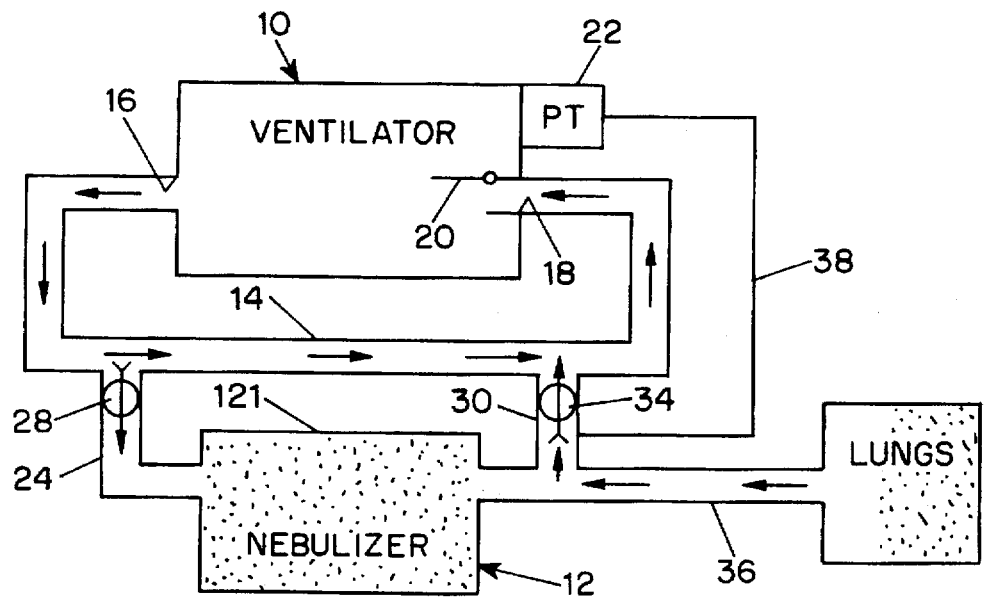

The apparatus of FIGS. 1 to 3 comprises a ventilator 10 of the continuous flow type that is used for neonates and infants and a conventional, commercially available ultrasonic nebulizer 12, such as a DeVilbiss "Aerosonic" nebulizer, connected in parallel with a series flow conduit 14 that leads from the gas delivery outlet 16 to the gas return inlet 18 of the ventilator 10. A return gas outlet valve 20 at the gas return inlet, from which expiration gas from the patient and series flow gas from the ventilator flow conduit 14 are discharged, is operated by a pressure transducer 22, as described below. A first conduit 24 is connected between the series conduit 14 and an inlet 26 to the nebulizer cap 121 and has a one-way valve 28 that permits gas to flow only from the series conduit to the nebulizer inlet. A second conduit 30 is connected between an outlet 52 from the nebulizer cap 121 and the series conduit 14 at a location downstream, with respect to the direction of gas flow through the series conduit from the ventilator delivery outlet, from the connection between the first conduit 24 and the series conduit 14. The second conduit 30 has a one-way valve 34 that permits gas to flow only from the lung to the series conduit 14. An endotracheal tube 36 is connected to the cap outlet 32, provides communication with the patient's lungs, and communicates with the second conduit 30 upstream from the one-way valve 34, with respect of the direction of gas flow to the series conduit. A pressure sensor conduit 38 is connected between the second conduit 30 at a location upstream from the one-way valve 34 in the second conduit, with respect of the direction of gas flow to the series conduit 14.

FIG. 1 illustrates the condition of the apparatus just prior to inspiration. The series conduit 14 serves as a direct flow path from the delivery outlet 16 to the return inlet 18 of the ventilator. At this time all gas flow is through the series conduit 14. The two parallel conduits 24 and 30 to the nebulizer cap 121 have no flow. The pressure sensor conduit 38 never receives flow; it transmits the gas pressure in the system back to the pressure transducer 22 in the ventilator. The pressure in the system is monitored by the pressure transducer, which in turn operates a valve 20 in the ventilator to regulate gas flow. Depending on the system pressure, the ventilator outlet valve 20 is either open or closed. In this phase, the valve 20 is open. The nebulizer 12 is nebulizing the drug solution, but the aerosolized drug remains in the nebulizer chamber because there is no gas flow through it.

FIG. 2 shows the flow conditions during inspiration. The ventilator cycles a selected number of breaths per minute. At the start of each cycle, the outlet valve 20 of the ventilator closes. Gas can no longer flow to the ventilator inlet 18 through the series conduit 14, and gas is forced to flow into the parallel conduit 24 connected to the nebulizer. The pressure from the incoming gas opens the one way valve 28, permitting gas to flow through the nebulizer. As the gas flows through the nebulizer chamber, it entrains the aerosolized drug and transports it out through the outlet 32 of the nebulizer cap and through the endotracheal tube 36 into the lungs. The one-way valve 34 in the parallel conduit 30 leading from the nebulizer outlet 32 blocks flow from the ventilator, forcing all gas flow through the nebulizer. This efficiently delivers drugs into the lungs during inspiration.

Near the end of inspiration, gas continues to flow into the lungs, which continue to expand but offer a resistance, raising the system pressure. When the pressure reaches a preset limit, usually between 12–18 cm $H_2O$, the outlet valve 20 in the ventilator opens, permitting the gas to once again flow through the ventilator. The patient's expanded lungs now begin to recoil for expiration. As shown in FIG. 3, gas flow is reversed and proceeds out the endotracheal tube 36 and up the parallel conduit 30. The one-way valve 28 in the parallel conduit 24 will not permit flow back through the nebulizer. All flow continues through the conduit 30 into the series conduit 14 and back to the ventilator, from which it is exhausted to the atmosphere through the outlet valve 20. The nebulizer continues to nebulize during this phase, but all aerosolized drug remains in the nebulizer because there is no flow through the nebulizer during expiration.

Figure 8:
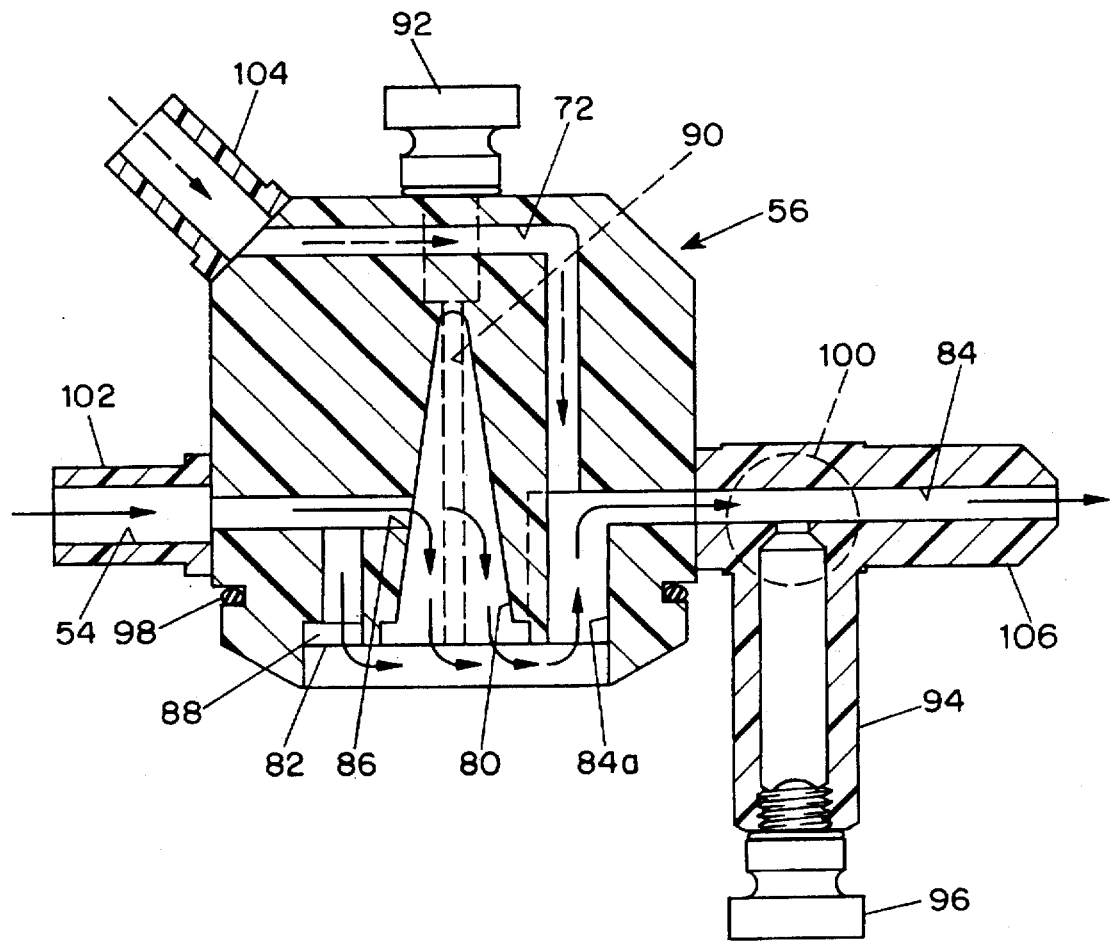
FIGS. 8 to 11 are, respectively, side cross-sectional, bottom plan, top plan and side elevational views of a cap for an ultrasonic nebulizer embodying several enhancements for improved function.
Figure 9:
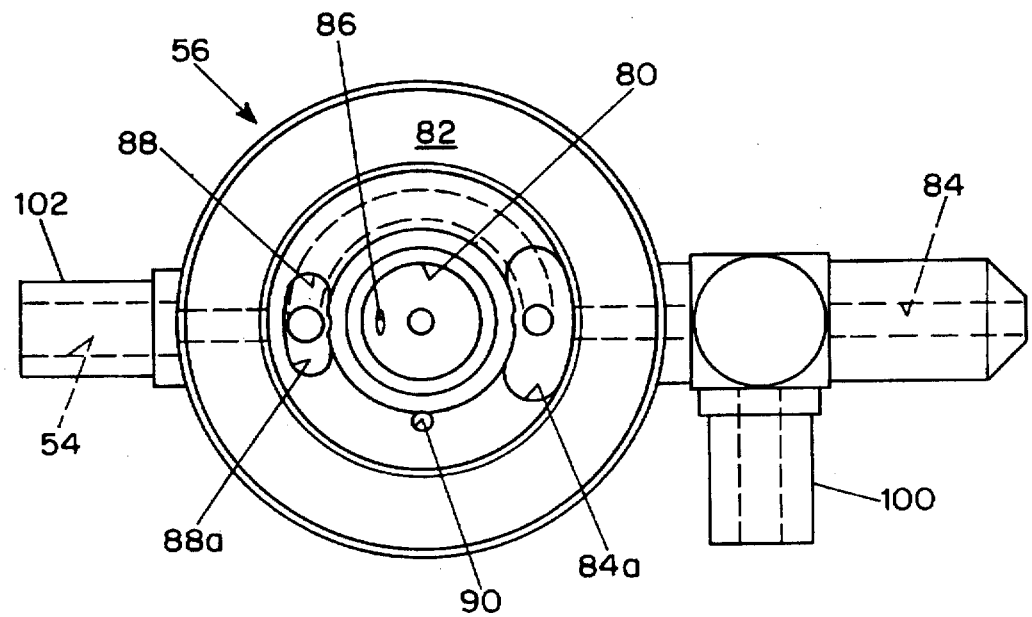
Figure 10:
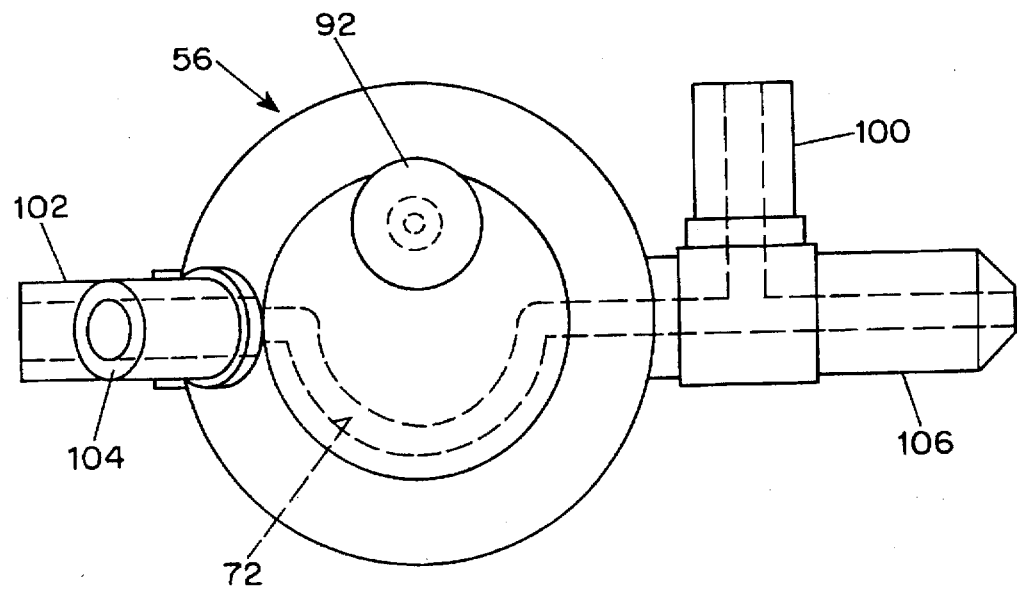
Figure 11:
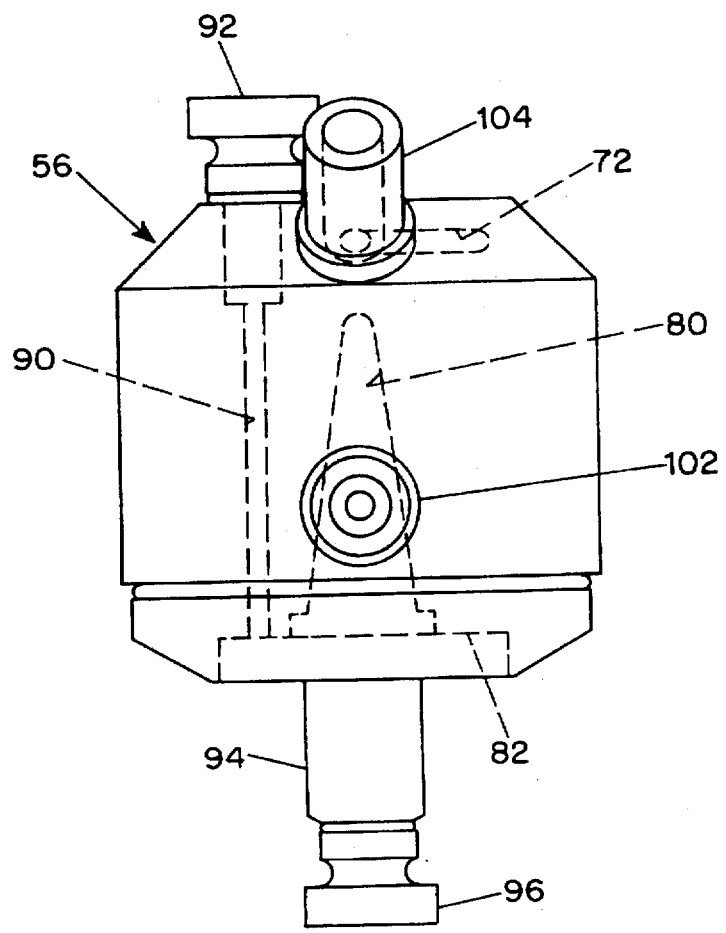

The importance of the series/parallel conduits and one-way valves can be appreciated during this phase. The ventilator generates a continuous flow of gas, yet none goes through the nebulizer. The flow is shunted via the series conduit, and expiration flow is through the conduit 30. This eliminates wasteful losses from the nebulizer. At present nebulizers are connected in series with the ventilator and drugs are lost through the flow system, inasmuch as no flow enters the lungs during this phase. The flow circuitry of the present invention solves this problem. After exhalation, the system returns to the state shown in FIG. 1. The ventilated breathing cycle repeats itself until all drug in the nebulizer has been aerosolized and delivered.

As shown in FIGS. 4 to 7, the flow system can to great advantage be further modified to maximally deposit drugs in the lung by providing a flow regulator 40 and associated flow paths between the ventilator and the endotracheal tube, which direct the inspiratory flow. An inlet 42 to the regulator 40 is connected to a conduit 44 leading from the ventilator outlet 16, which provides flow only from the ventilator to the regulator through a one-way valve 46 (depicted as a flapper valve). The flow regulator has two outlets 48 and 50*a*, 50*b* (the latter being a dual outlet), one of which 48 is connected by a conduit 52 to the inlet 54 of a nebulizer cap 56. The cap 56 is received in sealed relation on a base unit 58 of the nebulizer, which contains a vibrating crystal. A power supply (not shown) is connected by a power cord 62 to the base unit. The flow regulator 40 includes a slide valve 64, which is switched to provide two flow paths, one to the outlet 48 and the other to the dual outlets 50*a*, 50*b*, by a light-weight piston 66 that slides with a clearance along a tube 68 connected to the inlet 42. The dual outlets 50*a*, 50*b* are connected by conduits 70*a*, 70*b* to a bypass passage 72 in the cap 56, which provide a bypass flow path for gas from the ventilator to the endotracheal tube.

FIG. 4 illustrates the system at rest and just before inspiration. Gas is flowing through the series conduit 14, bypassing the nebulizer 56, 58. As described previously inspiration is initiated when the outlet valve 20 of the ventilator closes (see FIG. 2). Gas flow proceeds through the conduit 44, opening the one-way valve 46, and passes into the tube 68 of the regulator. The piston 66 in the tube 68 in flow regulator rises quickly and offers little resistance to upward movement. During upward movement of the piston, gas from the ventilator flows ahead of the piston and also bypasses it and thence flows through a hole 64*a* in the sleeve valve 64, through the conduit 52, and through the nebulizer chamber in the cap 56 (described below). The aerosol in the chamber is transported by the flow into the lungs of the patient. As the flow continues, the piston 66 rises along the tube 68 (see FIG. 5) and ultimately engages and lifts the sleeve valve 64 out of obstructing relation to lateral tubes 68*a*, 68*b* of the valve (see FIG. 6). Prior to this time, the sleeve valve 64 blocked the lateral tubes, forcing all gas from the ventilator to flow through the hole 64*a* and the nebulizer chamber, thus delivering the aerosolized drug to the patient's lungs.

In addition to opening the sleeve valve 64 to the branch tubes 68*a* and 68*b* of the regulator valve at the end of its upward excursion in the tube 68, the piston 66 closes the hole 64*a* in the valve, thereby stopping gas flow to the nebulizer. Opening of the lateral tubes 68*a*, 68*b* establishes a flow path to the endotracheal tube through the bypass 72 in the cap 56. Gas from the ventilator now flows through the bypass into the lungs. The gas flow through the bypass and into the lungs drives the aerosolized drug deep into the lungs and improves distribution of the drug in the lungs and deposition of the drugs on the surfaces in the lungs. Upon expiration, there is a lesser amount of aerosolized drug in the endotracheal tube and bronchi, thus less to be expelled upon exhalation. The drug has, therefore, been targeted predominantly to the alveoli which are the most peripheral areas of the lung.

Upon exhalation, as shown in FIG. 7 and as described above in connection with FIG. 3, the development of pressure in the lungs and an exhalation tube 74 leading from the endotracheal tube to the parallel conduit 14 of the ventilator, which has a one-way valve 76, causes the exhaust valve 20 to open. Gas flows from the lungs to the ventilator through the exhalation tube 74 and is discharged from the ventilator exhaust. Gas cannot back-flow through the nebulizer because of the one-way valve 46. During exhalation, the piston 66 falls by gravity back down to the bottom of the tube 68. The apparatus is now at rest and ready for the next inspiration.

A refinement not shown in the drawings is a means for adjusting the time period of the initial delivery through the tube 52. One way of doing so is to provide an adjustable lower stop in the tube 68 for the piston 66. The higher up in the tube the piston is set initially, the shorter the time of the initial phase of inspiration, and vice versa. Another way of changing the time period is to have pistons with different weights or sizes, which will change the velocity at which they travel up the tube propelled by the gas flow in the tube.

The apparatus of FIGS. 4 to 7 can be reconfigured to provide delivery of gas (air or oxygen or a mixture) to the lungs in the initial part of inspiration and delivery of the aerosolized drug during the final part of inspiration. This change requires only reversing the connection of the tubes 52 and 70*b*—i.e, connecting the tube 52 to the bypass 72 and connecting the tube 70*b* to the nebulizer chamber inlet 54. In the reconfigured mode, gas from the ventilator flows through the bypass and enters the lungs first, followed by the aerosolized drug from the nebulizer, and the drug tends to penetrate only as far as the bronchial passages.

The embodiments, as described up to this point, have been concerned with directing flow. Additional improvements in the apparatus involve the nebulizer cap 56. Caps for ultrasonic nebulizers currently in use are simply large holding chambers. Some have internal baffling or tubes with a plate or plane for impaction of the fluid geyser produced by a vibrating crystal on the bottom of the nebulizer. One aspect of the improved cap 56, which is shown in detail in FIGS. 8 to 11, is to provide an inverted (apex at the top) cone 80 as the top wall of the chamber in the cap above the vibrating crystal 60 (FIG. 4). The cone focuses the geyser and prevents splatter after impaction. The intensity of the cloud created is a function of the distance of the cone from the solution. In addition, a shield 82 around the base of the cone confines a small volume above the concavity of the base unit 58 of the nebulizer and further contains splattering and concentrates the cloud. For use with neonates and infants, the chamber size is about 20% of the volume of the chambers of caps currently in use. This not only encloses and holds down the aerosolized cloud, but also significantly decreases adhesion losses inside the nebulizer chamber. Aerosolized fluid droplets land and stick to inner surfaces of the chamber and remain on these surfaces due to surface tension. Fluid trapped in this manner becomes unavailable for further aerosolization. The smaller chamber curtails these losses.

Little attention has been paid to the porting of the nebulizer cap, which conventionally has been simply large holes connected to ventilator conduits or a mouthpiece. It is beneficial to restrict the outlet port of the nebulizer to a narrow, say, 4 mm diameter hole 84 (FIG. 8) which directly connects to the endotracheal tube. This greatly limits losses from the nebulizer dead space. Dead space is defined as chamber and conduit volumes filled with aerosolized drug that do not reach the lungs during each inspiration. The inlet porting to the chamber includes a port 86 in the wall of the cone 80, which creates a downflow of gas in the cone to sweep aerosol into the confined space between the cap and the base, and a port 88 in the shield 82. The ports 86 and 88 are diametrically opposite from the outlet 84. Enlarged portions 88a and 84a of the inlet and outlet ports provide for expanded inflow of gas and collected outflow, respectively, for more complete sweeping of the chamber volume.

The bypass 72 through the cap 56 joins the outlet 84 at the top of the enlarged portion outlet 84a. Gas flowing through the bypass does not entrain aerosol. The gas flows through the passage 84 into the lungs.

Other features of the cap include a fill passage 90 with a removable cap 92, which allows drugs to be introduced without removing the cap from the nebulizer; a collection trap 94 with a removable cap 96 for collecting and draining expired liquids; a sealing ring 98 that seals the cap to the base 58; a male coupling 100 for the exhalation tube; a male coupling 102 for the tube 52 (or 70a); a male coupling 104 for the tube 70a (or 52); a male coupling 106 for the endotracheal tube.

Figure 12:
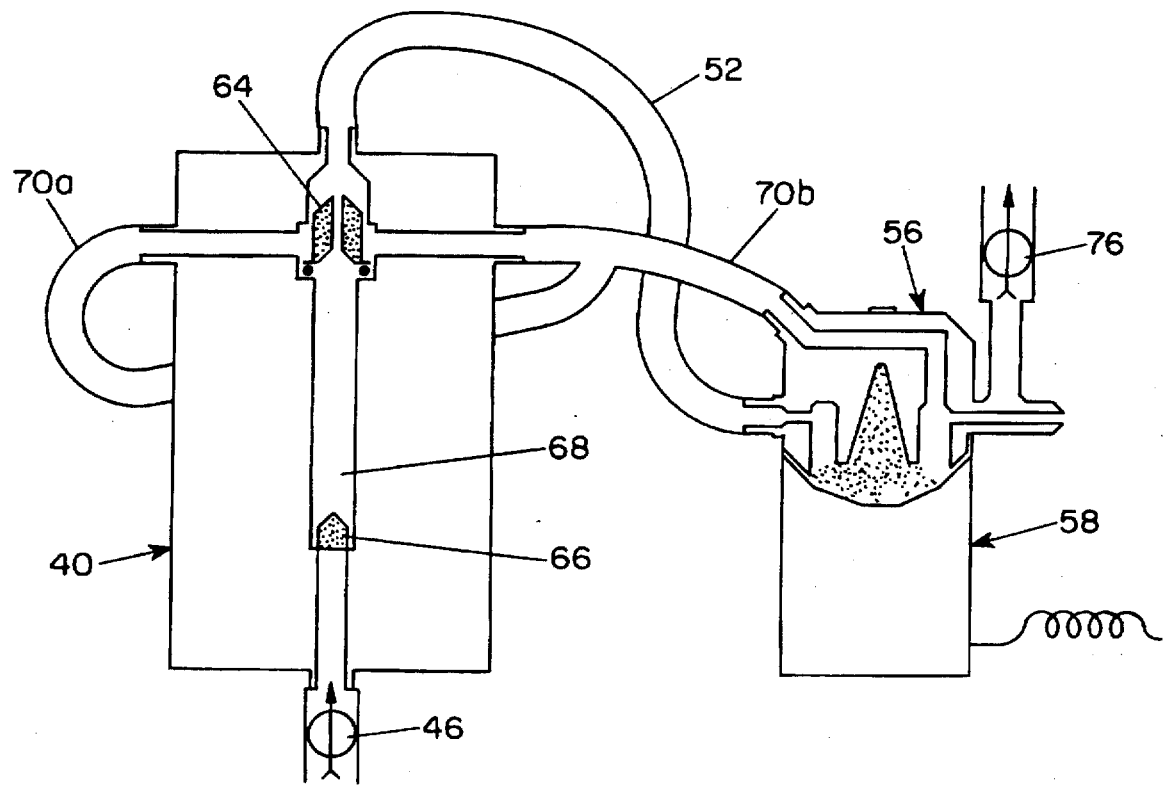
FIG. 12 is a schematic diagram of apparatus similar to that of FIGS. 4 to 7 for use in drug delivery by inhalation (natural breathing by the patient).
Figure 4:
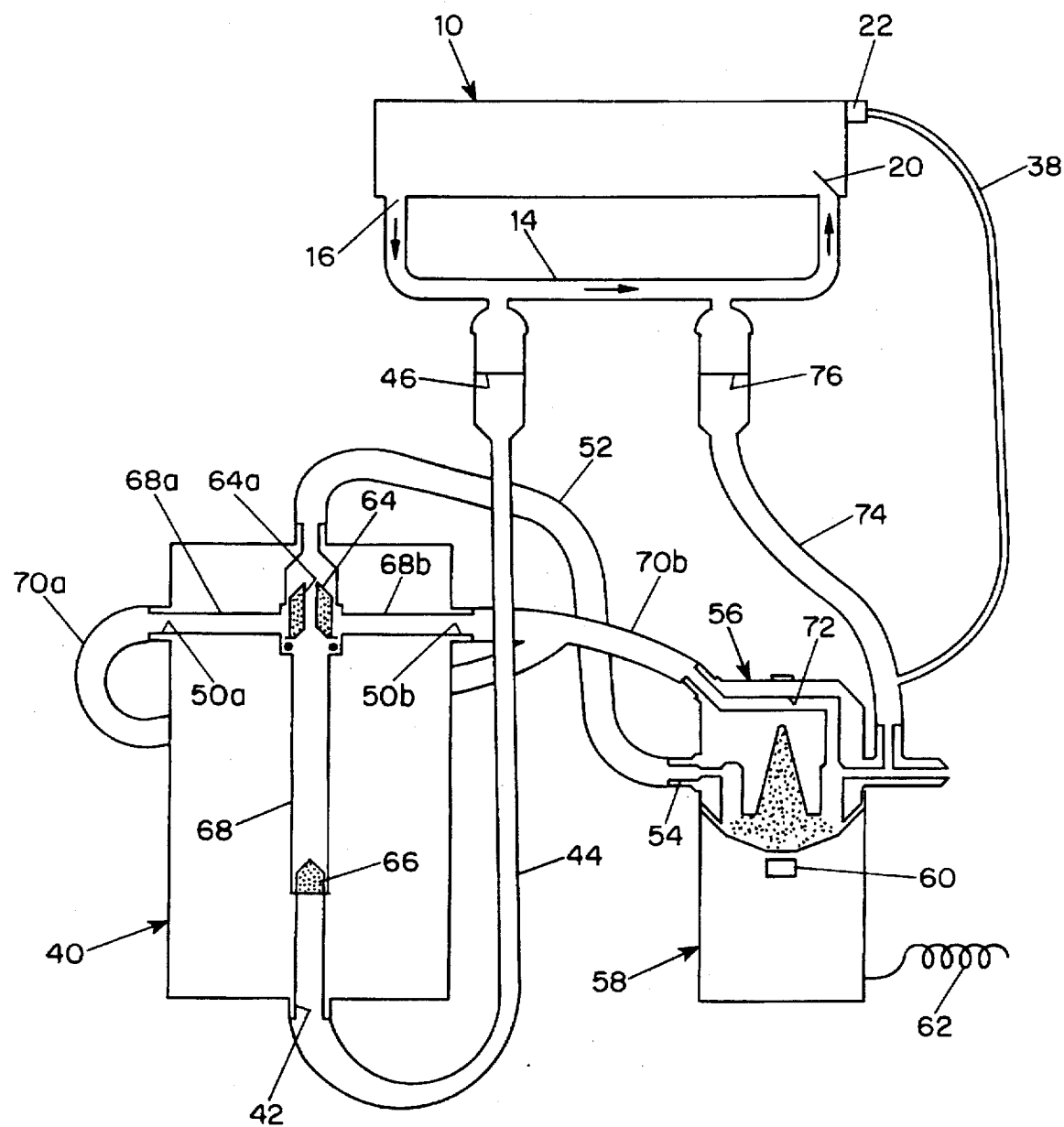
FIGS. 4 to 7 are schematic diagrams, also showing different phases of operation, of the apparatus of FIGS. 1 to 3, equipped with additional flow system enhancements.
Figure 5:
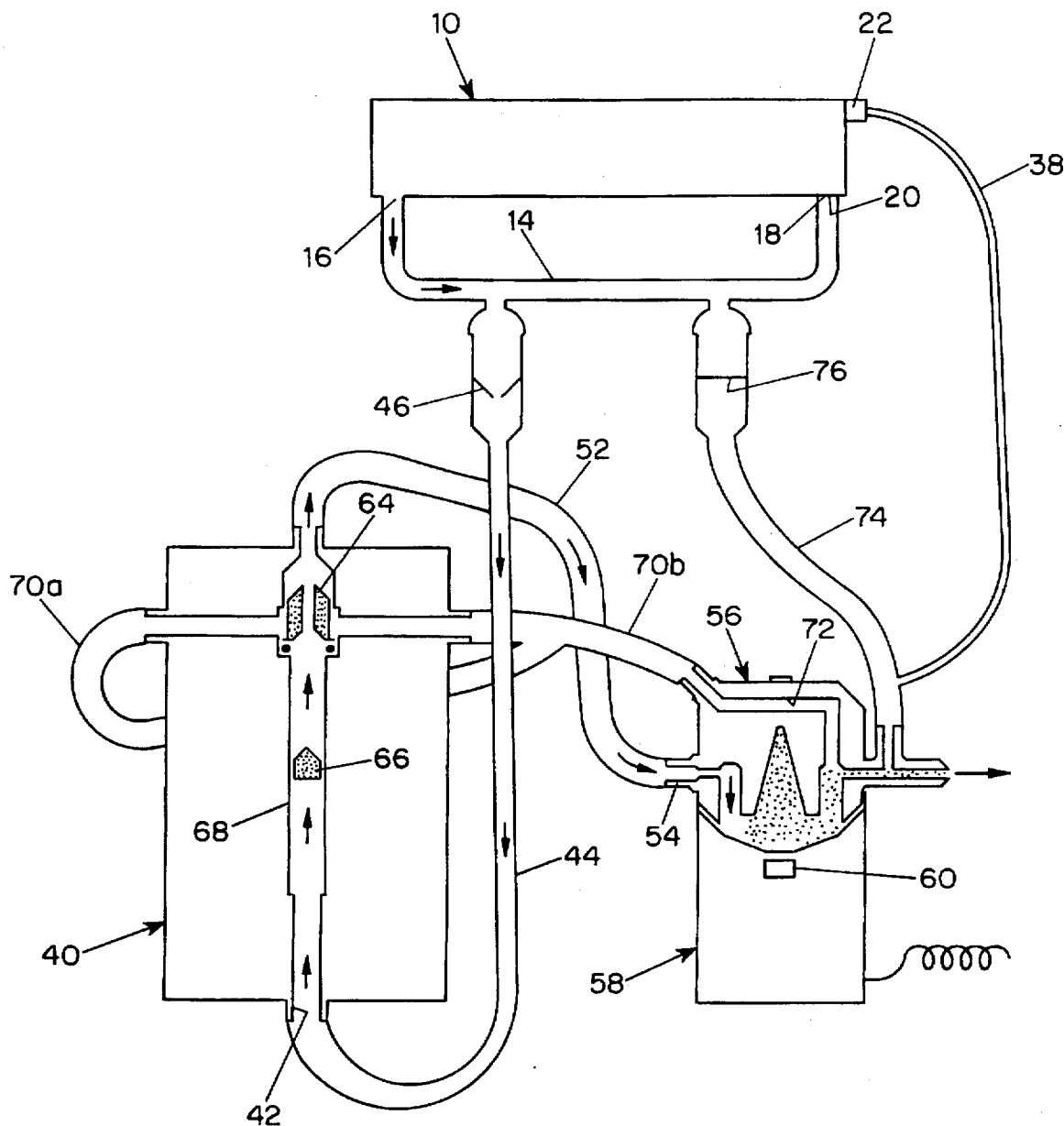
Figure 6:
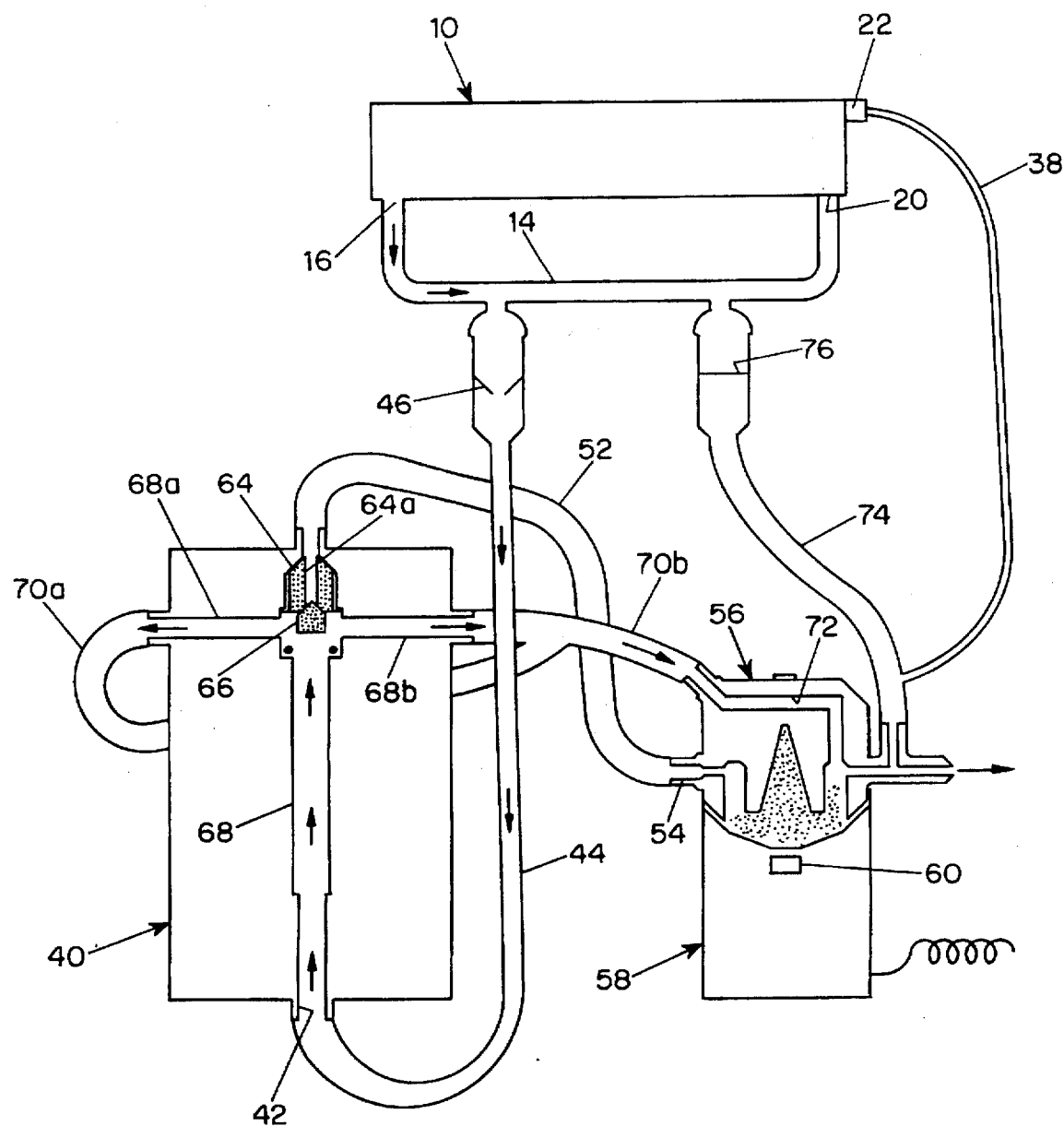
Figure 7:
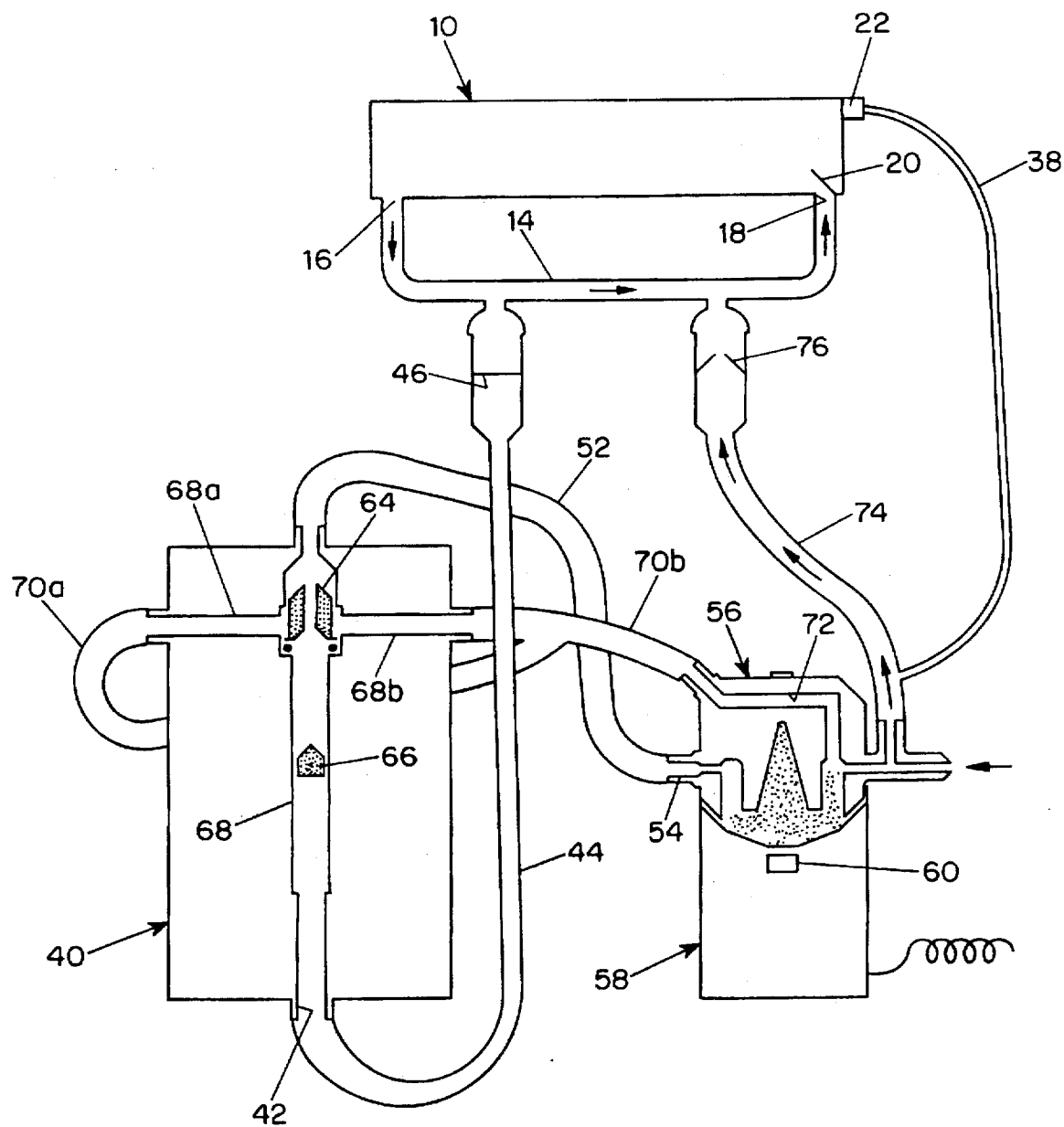

A nebulizer cap and flow regulation apparatus embodying the improvements of the present invention can also be adapted to patient inhalation by natural breathing (no ventilator). Indeed, the apparatus shown in FIGS. 4 to 7 can be used by simply disconnecting it from the ventilator, eliminating unnecessary tubing and substituting a mouthpiece for an endotracheal tube, as shown in 12. The operation of the inhalation apparatus of FIG. 12 is essentially the same as that of the system of FIG. 4 to 7, and reference may be made to the above description. The only difference is that inflows of the aerosolized drug and air are produced by the patient's inhalation rather than by a ventilator.

The system of the present invention can, of course, be adapted for adults. The flow regulator can be readily designed for inspiration (or inhalation) of larger volumes. The nebulizer chamber size can be expanded to accommodate a larger aerosol cloud. The outlet port and endotracheal tube adaptor (or mouthpiece) can be widened to adult size. The operation of the system will remain the same and will deliver drugs with even greater efficiency than in an infant.

The use of the apparatus of the present invention for drug delivery in infants and adults on ventilators and in infants and adults breathing normally offers an enormous improvement. The efficiency of drug delivery is many times that afforded by currently available apparatus. Because the nebulizer aerosolizes droplets of solution, it can deliver many types of drugs that can be dissolved or suspended in a liquid. These include antibiotics, bronchodilators, steroids and surfactants which are given for direct lung therapy. Aerosolized drugs for the heart represent a very important potential use. Aerosolized drugs deposited in the lungs will be absorbed by cells lining the internal surface areas of the lungs. These drugs will reach the heart on a first pass through the pulmonary vein because all the blood passing through the lungs is oxygenated and is transported in the pulmonary circulatory system directly to the heart before being disseminated to other organs and throughout the body in the systemic circulatory system. Because of the immediate route between lung and heart, it is postulated that inhaled drugs will serve as an efficient method of drug delivery to the heart. Absorption of drugs by the cells of the lung is a temporal process. Thus drugs will be delivered over time, supplying a constant dose rather than a bolus as occurs by injection.

The drawings are highly schematic in form. It is well within the ordinary skill of the art to design one-way valves, a flow regulator and a nebulizer cap so that they can be mass-produced by molding parts from suitable polymeric materials at relatively low cost. Currently available standard tubing and connectors can be used. The various components can be made in different sizes for infants and adults. In many cases, it is practical for drug companies to directly package their drugs with pre-assembled disposable units. The drug may be contained in the cap, the bottom of which is provided with a membrane for containing the drug. The membrane will nest in the cavity of the nebulizer base so that the drug can be aerosolized in situ by simply placing the cap on the base.

I claim:

1. Apparatus for delivering drugs to the lungs of a patient comprising a ventilator having a gas delivery outlet and a gas return inlet, a series conduit leading from the ventilator outlet to the gas return inlet, a return gas outlet valve at the gas return inlet, and a pressure transducer in the ventilator that is adapted to operate the ventilator return gas outlet valve in response to a pressure;

a nebulizer having means for forming an aerosol from a solution of a drug in a liquid and having an inlet and an outlet;

a first conduit connected between the series conduit and the nebulizer inlet and having a one-way valve permitting gas to flow only from the series conduit to the nebulizer inlet;

a second conduit connected between the nebulizer outlet and the series conduit at a location downstream, with respect to the direction of gas flow through the series conduit from the ventilator delivery outlet, from the connection between the first conduit and the series conduit, the second conduit having a one-way valve permitting gas to flow only from the nebulizer to the series conduit;

a pressure sensor conduit connected between the second conduit at a location upstream from the one-way valve in the second conduit, with respect of the direction of gas flow to the series conduit, and the pressure transducer so as to communicate the pressure at said location to the pressure transducer; and an endotracheal tube connected to the nebulizer outlet and communicating with the second conduit upstream from the one-way valve in the second conduit, with respect of the direction of gas flow to the series conduit.

2. Apparatus according to claim 1 and further comprising flow regulator means interposed in the first conduit to receive gas from the ventilator for regulating the flow of gas from the ventilator outlet to the nebulizer inlet.

3. Apparatus according to claim 2 wherein the regulator means supplies gas from the ventilator outlet to the nebulizer inlet during only a portion of each inspiration of the patient.

4. Apparatus according to claim 3 wherein the regulator means supplies gas to the nebulizer during an initial portion of each inspiration of the patient.

5. Apparatus according to claim 4 and further comprising a bypass conduit connected between the regulator means and the endotracheal tube and wherein the regulator means supplies gas from the ventilator to the bypass conduit during the portion of each inspiration of the patient when the gas from the ventilator is not being supplied to the nebulizer inlet.

6. Apparatus according to claim 5 and further comprising a bypass conduit connected between the regulator means and the endotracheal tube and wherein the regulator means supplies gas from the ventilator to the bypass conduit during the portion of each inspiration of the patient immediately after termination of the supply of gas from the ventilator to the nebulizer inlet.

7. Apparatus according to claim 1 wherein the nebulizer is an ultrasonic nebulizer having a vibrating crystal and a cap, the cap having a wall member presenting a downwardly facing conical surface having its apex centered above the vibrating crystal of the nebulizer.

8. Apparatus according to claim 7 wherein the nebulizer inlet includes a first inlet port in the conical surface of the wall member in spaced apart relation from the apex and the outlet from the cap includes an outlet port located proximate to the base of the conical surface and generally diametrically opposite from the cap inlet.

9. Apparatus according to claim 8 wherein the cap inlet further includes a second inlet port located proximate to the base of the conical surface and generally diametrically opposite from the cap outlet port.

10. Apparatus for delivering drugs to the lungs of a patient comprising a ventilator having a gas delivery outlet and a gas return inlet, a series conduit leading from the ventilator outlet to the gas return inlet, a return gas outlet valve at the gas return inlet, and a pressure transducer in the ventilator that is adapted to operate the ventilator outlet valve in response to a pressure;

an ultrasonic nebulizer having means including a vibrating crystal for forming an aerosol from a solution of a drug in a liquid and a cap defining a chamber for the aerosol and having an inlet and an outlet;

a first conduit having an inlet end connected to the series conduit;

a one-way valve in the first conduit permitting gas to flow only from the series conduit;

a second conduit having an outlet end connected to the series conduit at a location downstream, with respect to the direction of gas flow through the series conduit from the ventilator delivery outlet, from the connection between the first conduit and the series conduit;

a one-way valve in the second conduit permitting gas to flow only to the series conduit;

a pressure sensor conduit connected between the second conduit at a location upstream from the one-way valve in the second conduit, with respect of the direction of gas flow to the series conduit, and the pressure sensor and communicating the pressure at said location to the pressure transducer;

an endotracheal tube connected to the cap outlet and communicating with the second conduit upstream from the one-way valve in the second conduit, with respect of the direction of gas flow to the series conduit;

and flow regulator means having an inlet connected to the first conduit to receive gas from the ventilator, a first outlet connected to a third conduit, and a second outlet connected to a fourth conduit, one of the third and forth conduits being connected to the cap inlet and the other of the third and fourth conduits being connected to the endotracheal tube, and valve means for conducting gas from the inlet to the first outlet for an initial portion of each inspiration of the patient and for conducting gas to the second outlet during a final portion of each inspiration of the patient.

11. Apparatus according to claim 10 wherein the valve means of the flow regulator means is responsive to gas flow from the ventilator during each inspiration of the patient.

12. Apparatus according to claim 11 wherein the valve means of the flow regulator means includes a movable piston propelled by gas flow from the ventilator and a valve member for changing the flow between the first outlet and the second outlet of the regulator means.

13. Apparatus according to claim 10 wherein the nebulizer cap has a wall member presenting a downwardly facing conical surface having its apex centered above the vibrating crystal of the nebulizer.

14. Apparatus according to claim 13 wherein the cap inlet includes a first inlet port in the conical surface of the wall member in spaced apart relation from the apex and the outlet from the cap includes an outlet port located proximate to the base of the conical surface and generally diametrically opposite from the cap inlet.

15. Apparatus according to claim 14 wherein the cap inlet further includes a second inlet port located proximate to the base of the conical surface and generally diametrically opposite from the cap outlet port.

16. Apparatus for delivering drugs to the lungs of a patient comprising a ventilator having a gas delivery outlet and a gas return inlet, a series conduit leading from the ventilator outlet to the gas return inlet, a return gas outlet valve at the gas return inlet, and a pressure transducer in the ventilator that is adapted to operate the ventilator return gas outlet valve in response to a pressure;

an ultrasonic nebulizer having means including a vibrating crystal for forming an aerosol from a solution of a drug in a liquid and a cap defining a chamber for the aerosol and having an inlet and an outlet;

an endotracheal tube connected to the cap outlet and adapted to be inserted into the trachea of a patient;

a bypass conduit connected to the endotracheal tube downstream from the cap outlet; and flow regulating means for regulating gas flows to and from the endotracheal tube including means for establishing a first flow path for a first predetermined time period for conducting a gas from the ventilator outlet through the nebulizer cap to the endotracheal tube, means for establishing a second flow path for a second predetermined time period for conducting a gas from the ventilator outlet through the bypass conduit to the endotracheal tube, and means for establishing a third flow path for a third predetermined time period for conducting a gas from the endotracheal tube to the ventilator gas return inlet.

17. Apparatus according to claim 16 wherein the means for establishing the first flow path includes a first conduit connected to the series conduit, a second conduit connected to the nebulizer cap inlet, a one-way valve in the first conduit permitting gas to flow through the first conduit only from the series conduit, and controllable valve means for connecting the first and second conduits.

18. Apparatus according to claim 16 wherein the controllable valve means includes is a sleeve valve.

19. Apparatus according to claim 18 wherein the controllable valve means further includes a piston driven by gas flow from the ventilator through the first flow path for changing the position of the sleeve valve.

20. Apparatus according to claim 16 wherein the means for establishing the second flow path includes a first conduit connected to the series conduit, a one-way valve in the first conduit permitting gas to flow through the first conduit only from the series conduit, the bypass conduit and a controllable valve connecting the first conduit and the bypass conduit.

21. Apparatus according to claim 20 wherein the controllable valve is a sleeve valve.

22. Apparatus according to claim 21 wherein the controllable valve means further includes a piston driven by gas flow from the ventilator through the second flow path for changing the position of the sleeve valve.

23. Apparatus according to claim 16 wherein the means for establishing the third flow path includes an exhalation conduit connected between the endotracheal tube and the series conduit, and a one-way valve in the exhalation conduit permitting gas to flow only from the endotracheal tube to the series conduit.

24. Apparatus according to claim 16 wherein the nebulizer cap has a wall member presenting a downwardly facing conical surface having its apex centered above a vibrating crystal of the nebulizer.

25. Apparatus according to claim 16 wherein the cap inlet includes a first inlet port in the conical surface of the wall member in spaced apart relation from the apex and the outlet from the cap includes an outlet port located proximate to the base of the conical surface and generally diametrically opposite from the cap inlet.

26. Apparatus according to claim 25 wherein the cap inlet further includes a second inlet port located proximate to the base of the conical surface and generally diametrically opposite from the cap outlet port.

27. In an ultrasonic nebulizer having means including a vibrating crystal for forming an aerosol from a solution of a drug in a liquid, a cap defining a chamber for the aerosol and having an inlet for receiving ambient air and an outlet for discharging a mixture of air and the aerosol, and a mouthpiece connected to the cap outlet, the improvement comprising a first conduit having an outlet connected to the mouthpiece, a second conduit having an outlet connected to the cap inlet, flow regulator means having an inlet for ambient air, a one-way valve in the inlet for permitting ambient air to flow only to the inlet, first and second outlets connected respectively to inlets to the first and second conduits for controlling the flow of air to the first and second conduits such that air flows to one of the first and second conduits during an initial portion of each inhalation by a patient using the nebulizer and air flows to the other of the first and second conduits during the remaining portion of each inhalation by the patient, and an exhalation port connected to the mouthpiece and having a one-way valve for permitting gas to flow only from the mouthpiece upon each exhalation by the patient.

28. The improvement according to claim 27 wherein the nebulizer cap has a wall member presenting a downwardly facing conical surface having its apex centered above a vibrating crystal of the nebulizer.

29. Apparatus according to claim 28 wherein the cap inlet includes a first inlet port in the conical surface of the wall member in spaced apart relation from the apex and the outlet from the cap includes an outlet port located proximate to the base of the conical surface and generally diametrically opposite from the cap inlet.

30. Apparatus according to claim 29 wherein the cap inlet further includes a second inlet port located proximate to the base of the conical surface and generally diametrically opposite from the cap outlet port.

31. Apparatus according to claim 30 wherein the first conduit includes a portion of the cap outlet.

32. Apparatus according to claim 31 wherein the first conduit includes a passage in the cap having a port communicating with the cap outlet port.

* * * * *